United States Patent
Castor

(10) Patent No.: US 10,828,276 B2
(45) Date of Patent: Nov. 10, 2020

(54) COMBINATION THERAPEUTICS AND METHODS FOR THE TREATMENT OF NEURODEGENERATIVE AND OTHER DISEASES

(71) Applicant: APHIOS CORPORATION, Woburn, MA (US)

(72) Inventor: Trevor Percival Castor, Arlington, MA (US)

(*) Notice: Subject to any disclaimer, the term of this patent is extended or adjusted under 35 U.S.C. 154(b) by 0 days.

(21) Appl. No.: 14/646,817

(22) PCT Filed: Nov. 26, 2013

(86) PCT No.: PCT/US2013/072076
§ 371 (c)(1),
(2) Date: May 22, 2015

(87) PCT Pub. No.: WO2014/085494
PCT Pub. Date: Jun. 5, 2014

(65) Prior Publication Data
US 2015/0297555 A1  Oct. 22, 2015

Related U.S. Application Data

(60) Provisional application No. 61/730,761, filed on Nov. 28, 2012.

(51) Int. Cl.
| | |
|---|---|
| *A61K 31/203* | (2006.01) |
| *A61K 31/352* | (2006.01) |
| *A61K 31/07* | (2006.01) |
| *A61K 31/22* | (2006.01) |
| *A61K 31/23* | (2006.01) |
| *A61K 31/365* | (2006.01) |
| *A61K 9/51* | (2006.01) |
| *A61K 9/48* | (2006.01) |
| *A61K 9/00* | (2006.01) |

(52) U.S. Cl.
CPC .......... *A61K 31/352* (2013.01); *A61K 9/4858* (2013.01); *A61K 9/4875* (2013.01); *A61K 9/5153* (2013.01); *A61K 31/203* (2013.01); *A61K 31/365* (2013.01); *A61K 9/0095* (2013.01)

(58) Field of Classification Search
CPC .. A61K 31/352; A61K 9/4858; A61K 9/4875; A61K 9/5153; A61K 31/203; A61K 31/365
See application file for complete search history.

(56) References Cited

U.S. PATENT DOCUMENTS

| | | |
|---|---|---|
| 4,560,774 A | 12/1985 | Pettit et al. |
| 4,611,066 A | 9/1986 | Pettit et al. |
| 5,641,745 A | 6/1997 | Ramtoola |
| 5,736,542 A | 4/1998 | Henry et al. |
| 5,750,709 A | 5/1998 | Castor |
| 5,854,064 A | 12/1998 | Castor et al. |
| 6,221,153 B1 | 4/2001 | Castor et al. |
| 6,228,843 B1 | 5/2001 | Dempsey |
| 6,407,058 B1 | 6/2002 | Staddon et al. |
| 6,624,189 B2 | 9/2003 | Wender et al. |
| 9,034,347 B2 | 5/2015 | Castor et al. |
| 2002/0061303 A1* | 5/2002 | Singh ............... A61K 31/00 424/94.63 |
| 2003/0171356 A1 | 9/2003 | Etcheberrigaray et al. |
| 2003/0199469 A1 | 10/2003 | Schwartz et al. |
| 2006/0154893 A1 | 7/2006 | Beaudet et al. |
| 2006/0165987 A1* | 7/2006 | Hildgen ............... A61K 9/5153 428/402.2 |
| 2007/0190163 A1 | 8/2007 | Malaknov et al. |
| 2008/0004332 A1 | 1/2008 | Alkon |
| 2008/0207742 A1 | 8/2008 | Zohar et al. |
| 2009/0270308 A1* | 10/2009 | Libin |
| 2009/0270492 A1 | 10/2009 | Wender |
| 2009/0306225 A1 | 12/2009 | Lichter et al. |
| 2010/0166806 A1 | 7/2010 | Castor |
| 2010/0168219 A1 | 7/2010 | Alexander |
| 2011/0129450 A1 | 6/2011 | Lazarov et al. |
| 2012/0309818 A1 | 12/2012 | Alexander et al. |
| 2015/0094363 A1 | 4/2015 | Alexander et al. |
| 2015/0246000 A1 | 9/2015 | Castor et al. |

(Continued)

FOREIGN PATENT DOCUMENTS

| | | |
|---|---|---|
| JP | 2005-535660 A | 11/2005 |
| JP | 2007-535563 A | 12/2007 |
| WO | 2004/004641 A2 | 1/2004 |

(Continued)

OTHER PUBLICATIONS

IUPAC GoldBook definition of biopolymer (https://goldbook.iupac.org/html/B/B00661.html,1 page, accessed Oct. 18, 2018) (Year: 2018).*

Dale et al., Comparison of effects of bryostatins 1 and 2 and 12-O-tetradecanoylphorbol-13-acetate on protein kinase C activity in A549 human lung carcinoma cells. Cancer Res. Jun. 15, 1989;49(12):3242-5.

Hale et al., The chemistry and biology of the bryostatin antitumor macrolides. Natural Product Reports. 2002;19(4):413-453.

Manning, Identifying byrostatins and potential precursors from the bryozoan Bugula neritina. Natural Product Research. 2005;19:467-491.

Mehla et al., Bryostatin modulates latent HIV-1 infection via PKC and AMPK signaling but inhibits acute infection in a receptor independent manner. PLoS One. Jun. 16, 2010;5(6):e11160. 15 pages.

(Continued)

*Primary Examiner* — Alma Pipic

(57) ABSTRACT

Embodiments of the present invention are directed to the administration of bryostatins and bryostatins and retinoids for the treatment of disease responsive to increases in alpha secretase activity. Inventions of the present application are directed to the treatment of neuro-degenerative diseases such as Hutchinson Disease, Parkinson's disease, Down's syndrome and Alzheimer's disease and virus latency diseases such as HIV and Herpes, cancers such as prostate, melanomas, lymphomas and renal cancers, esophageal and opthalmic diseases such as glaucoma.

18 Claims, 4 Drawing Sheets

(56) References Cited

U.S. PATENT DOCUMENTS

2015/0291616 A1    10/2015    Castor
2015/0297555 A1    10/2015    Castor

FOREIGN PATENT DOCUMENTS

WO    2009/129361 A2      10/2009
WO    2010/144499 A2 *    12/2010
WO    2013/071282 A1       5/2013

OTHER PUBLICATIONS

Pettit et al., Structure of the *Bugula neritina* (Marine Bryozoa) Antineoplastic Component Bryostatin 3. J. Org. Chem. 1983;48:5354-5356.

International Search Report and Written Opinion for Application No. PCT/US2013/072076, dated Apr. 15, 2014. 16 pages.

Stone et al., "The Combination of All-Trans Retinoic Acid (Atra) and Bryostatin 1 (Bryo) Induces Monocytic Differentiation (Md) in Human Myeloid Leukemia", Leukemia Research, 1997, 21(1), Supplement 1, S24.

Carpenter et al. (2008) "Endothelial PKC delta activation attenuates neutrophil transendothelial migration," Inflammatory Research. 57(5):216-229.

Healy et al. (2006) "Neutrophil transendothelial migration potential predicts rejection severity in human cardiac transplantation," European Journal of Cardio-thoracic Surgery. 29(5):760-766.

Jordan et al (1999) "The role of neutrophils in myocardial ischemia-reperfusion injury," Cardiovascular Research. 43(4):860-878.

Lopanik et al., Structure of bryostatin 20: a symbiont-produced chemical defense for larvae of the host bryozoan, Bugula neritina. J Nat Prod. Aug. 2004;67(8):1412-4.

Moreno et al. (2006) "Neovascularization in human atherosclerosis," Circulation. 113(18):2245-2252.

Pettit et al., Antineoplastic Agents 100. The Marine Bryozoan Amathia Convoluta. Tetrahedron. 1985;41(6):985-994.

Pettit et al., Antineoplastic agents. 340. Isolation and structural elucidation of bryostatins 16-18. J Nat Prod. Mar. 1996;59(3):286-9.

Pettit et al., Isolation and Structure of Bryostatin 1. J Am Chem Soc. 1982;104:6846-6848.

Pettit et al., Isolation and structure of bryostatin 9. J Nat Prod. Jul.-Aug. 1986;49(4):661-4.

Pettit et al., Isolation and Structure of Bryostatins 10 and 11. J Org Chem. 1987;52:2848-2854.

Pettit et al., Isolation and Structure of Bryostatins 12 and 13. J Org Chem. 1987;52:2854-2860.

Pettit et al., Isolation and Structure of Bryostatins 14 and 15. Tetrahedron. 1991;47(22):3601-3610.

Pettit et al., Isolation and structure of bryostatins 5-7. Can J Chem. 1985;63:1204-1208.

Pettit et al., Structure of Bryostatin 4. An Important Antineoplastic Constituent of Geographically Diverse Bugula neritina (Bryozoa). J Am Chem Soc. 1984;106:6768-6771.

Pettit et al., The Structure of Bryostatin 2 from the Marine Bryozoan Bugula Neritina. Journal of Natural Products. Jul.-Aug. 1983;46(4):528-531.

Stone et al., A phase IIb trial of all-trans retinoic acid (ATRA) combined with bryostatin 1 (BRYO) in patients (pts) with myelodysplastic syndromes (MDS) and acute myeloid leukemia (AML). Blood. 2000;96(11, Part 2):265b, 42nd Annual Meeting of the American Society of Hematology, (abstract) BIOSIS [online] [retrieved on Oct. 18, 2017] BIOSIS.

Sodhi et al., All-trans retinoic acid rescues memory deficits and neuropathological changes in mouse model of streptozotocin-induced dementia of Alzheimer's type. Prog Neuropsychopharmacol Biol Psychiatry. Jan. 10, 2013;40:38-46.

Koryakina et al., Regulation of secretases by all-trans-retinoic acid. FEBS J. May 2009;276(9):2645-2655.

* cited by examiner

COMBINATION THERAPEUTICS AND METHODS FOR THE TREATMENT OF NEURODEGENERATIVE AND OTHER DISEASES

RELATED APPLICATIONS

This application is a 35 U.S.C. § 371 filing of International Application No. PCT/US2013/072076, filed Nov. 26, 2013, which claims priority to U.S. Patent Application No. 61/730,761, filed Nov. 28, 2012, each of which is incorporated herein by reference in its entirety.

STATEMENT REGARDING FEDERAL SUPPORT

This invention was made with Federal support including National Institutes of Health Grant No. 1R44AG034760-01A1.

FIELD OF INVENTION

Inventions of the present application are directed to the treatment of neuro-degenerative diseases such as Hutchinson Disease, Parkinson's disease, Down's syndrome and Alzheimer's disease and virus latency diseases such as HIV and Herpes, cancers such as prostate, melanomas, lymphomas and renal cancers, esophageal and opthalmic diseases such as glaucoma.

BACKGROUND OF THE INVENTION

Neurodegenerative diseases, such as Alzheimer's disease, Hutchinson's Disease, Parkinson's disease, Kuru, Creutzfeldt-Jakob disease and other spongiform encephalopathies remain major health problems. With respect to Alzheimer's, Hutchinson's and Parkinson's diseases, these diseases tend to manifest themselves in older individuals and as the diseases progress; the afflicted individuals are less able to care for themselves. With respect to cancers such as, by way of example, without limitation, prostate cancer, Bryostatin 1 inhibits phorbol ester-induced apoptosis in prostate cancer cells by differentially modulating protein kinase C (PKC) delta translocation and preventing PKCdelta-mediated release of tumor necrosis factor-alpha. With respect to virus latency diseases such as HIV latency, Bryostatin-1, as well as many PKC agonists, activates cellular transcription factors such as NF-kB that binds the HIV-1 promoter and regulates its transcriptional activity. In HIV-1 latency the viral promoter is less accessible to cellular transcription factors because nuclear histones surrounding the viral promoter are deacetylated (compacted chromatin). Thus HDAC inhibitors may increase the aceytation of histones (relaxed chromatin) and then transcription factors may have an easy access to the HIV promoter. With respect to opthalmic disease, such as by way of example, without limitation, glaucoma, the presence of beta amyloid is associated with elevated intra ocular pressure. Currently there are very limited means to treat these diseases.

It is therefore highly desirable to have effective therapeutics, combination therapeutics that act synergistically, effective methods of formulation and simple methods of administration (e.g. oral formulations) without the need for specially trained healthcare providers.

SUMMARY OF THE INVENTION

Embodiments of the present invention are directed to single and combination therapies, drug delivery systems, dosage forms and methods for the treatment of neurodegenerative diseases, cancers, viral latencies and optical diseases. The neurodegenerative diseases which are the object of treatment in the present invention are exemplified by Alzheimer's disease, Hutchinson's Disease, Parkinson's disease, Kuru, Creutzfeldt-Jakob disease, Down's syndrome and spongiform encephalopathies. Other diseases include cancers such as prostate cancer and viral latencies such as HIV and herpes. The embodiments directed to an article of manufacture comprise a dosage form comprising an effective amount of a byostatin or Bryoid with an effective amount of a Retinoid. As used herein, the term "dosage form" refers to a means for administering a drug, such as by way of example, without limitation, capsules, tablets, pills, films, ointments, creams, solutions, suspensions, aerosols, pastes, drops, suppositories, powders for reconstitution, injectables, intravenous solutions and the like.

As used herein, the term "a bryostatin" or "Bryoid" refers to any and all bryostatins and derivatives thereof. Twenty bryostatins have been identified and certain examples feature a bryostatin that is bryostatin-1. Embodiments of the present invention feature a first Bryoid composition having a molecular weight of approximately 896-898 Amu (Mass+Sodium) having a purity of approximately 50% to a crystal forming purity. The first Bryoid composition can also be characterized as a Bryoid compound having a molecular weight of approximately 873-875 Amu (monoisotopic mass) having a purity of approximately 50% and a crystal forming purity. The first Bryoid composition has a measured mass plus sodium of 897.2 Amu and a measured monoisotopic mass of 874.2 Amu. The detailed discussion which follows will refer to this Bryoid as B10.

Embodiments of the present invention feature a second Bryoid composition having a molecular weight of approximately 910-912 Amu (Mass+Sodium) having a purity of approximately 50% to a crystal forming purity. The second Bryoid composition can also be characterized as a Bryoid compound having a molecular weight of approximately 888-890 Amu (monoisotopic mass) having a purity of approximately 50% and a crystal forming purity. The second Bryoid composition has a measured mass plus sodium of 911.5 Amu and a measured monoisotopic mass of 888.9 Amu. The detailed discussion which follows will refer to this Bryoid as B12.

Embodiments of the present invention feature a third Bryoid composition having a molecular weight of approximately 868-870 Amu (Mass+Sodium) having a purity of approximately 50% to a crystal forming purity. The third Bryoid composition can also be characterized as a Bryoid compound having a molecular weight of approximately 846-848 Amu (monoisotopic mass) having a purity of approximately 50% and a crystal forming purity. The third Bryoid composition has a measured mass plus sodium of 869.5 Amu and a measured monoisotopic mass of 846.6 Amu. The detailed discussion which follows will refer to this Bryoid as B14B.

Embodiments of the present invention feature a fourth Bryoid composition having a molecular weight of approximately 895-897 Amu (Mass+Sodium) having a purity of approximately 50% to a crystal forming purity. The fourth Bryoid composition can also be characterized as a Bryoid compound having a molecular weight of approximately 872-874 Amu (monoisotopic mass) having a purity of approximately 50% and a crystal forming purity. The fourth Bryoid composition has a measured mass plus sodium of 895.5 Amu and a measured monoisotopic mass of 872.6 Amu. The detailed discussion which follows will refer to this Bryoid as B14C.

These Bryoid compounds of the present invention have molecular weights that are different than the molecular weights of bryostatins 1-20.

As used herein, crystal forming purity means the composition has a purity which enables the composition to form crystals. Normally, such purity is greater than 90%, and more often greater than 95% purity. Examples presented in this application feature compositions having a purity greater than 99%. Crystal purity would comprise compositions in which no impurities can be detected, but is not so limited.

The first Bryoid, second Bryoid, third Bryoid, and fourth Bryoid described above are the subject of a co-pending patent application of the present inventor and applicant filed Nov. 27, 2012, serial number U.S. 61/730,227. The entire contents of the co-pending application are incorporated by reference.

Embodiments of the present invention feature a Bryoid present in an amount to stimulate the production of alpha secretase. For example, a Bryoid is present for administration in a dose of 0.1-50 micrograms per square meter of surface area per week. Another embodiment of the present invention features a Bryoid present for administration in a dose of 5-10 micrograms per square meter of surface area per week.

Further embodiments of the article of manufacture comprise a Retinoid. The Retinoid is bioavailable in an oral form and selected from the group comprising retinoic acid, retinol, retinol acetate, retinol palmitate, 13-cis-retinoic acid, and bexarotene. The Examples will feature the retinoid, retinoic acid. The Examples feature the Retinoid in an amount to increase expression of alpha secretase. For example, without limitation, the retinoid is present in a dose of 1.0-240 mg per day.

Embodiments of the present invention feature nanospheres comprising a biopolymer which is resistant to acid. For example, without limitation, one biopolymer is a poly (D, L-lactide-coglycoside). This biopolymer has two components. Embodiments of the present invention feature a poly (D, L-lactide-co-glycoside) having a ratio of lactide and glycoside of 25-75% lactide with the remaining comprising glycoside. A common ratio is 50:50 lactide to glycoside as determined by weight. This biopolymer is resistant to gastric acid degradation and allows oral delivery of the drug to the small intestine for absorption. Nanospheres are about 1 to 1000 nanometers in diameter.

Embodiments of the present invention feature spheres that are lyophilized for reconstitution in an aqueous solution. Another embodiment features spheres held in suspension for oral administration and/or held in an oral dosage form selected from the group of tablets, capsules, gel caps, and powders. Suspensions for oral administration are preferably flavored to improve patient acceptance.

A further embodiment of the present invention is directed to a method of treating neuro-degenerative disease. The method comprises the steps of administering an effective amount of a bryostatin held in a plurality of spheres, each sphere comprising a biopolymer and bryostatin, and each sphere having a diameter of one to 1000 nanometers.

Embodiments of the present method feature a bryostatin selected from the group consisting of Bryostatins 1-20. Certain examples feature a bryostatin that is bryostatin-1. Several bryostatins of great potency are bryostatin-3; and the first Bryoid, second Bryoid and third bryoid referenced above.

Embodiments of the present invention feature bryostatin administered in an amount to stimulate the production of alpha secretase. For example, bryostatin is administered in a dose of 0.1-50 micrograms per square meter of surface area per week. Another embodiment of the present invention features a bryostatin administered in a dose of 5-10 micrograms per square meter of surface area per week.

Further embodiments of the method comprise co-administration of a retinoid. The retinoid is bioavailable in an oral form and selected from the group comprising retinoic acid, retinol, retinol acetate, retinol palmitate, 13-cis-retinoic acid, and bexarotene. The Examples will feature the retinoid, retinoic acid. The Examples feature the retinoid in an amount to increase expression of alpha secretase. For example, without limitation, the retinoid is administered in a dose of 1.0-240 mg per day.

One embodiment of the present invention features a biopolymer which is resistant to acid. For example, without limitation, one acid resistant biopolymer is a poly (D, L-lactide-coglycoside). Poly (D, L-lactide-co-glycoside) has a ratio of lactide and glycoside. A preferred ratio is 25-75% lactide with the remaining comprising glycoside.

Preferably, the microspheres are lyophilized for reconstitution in an aqueous solution, or held in suspension for oral administration or held in an oral dosage form selected from the group of tablets, capsules, gel caps, and powders.

As a further article of manufacture, embodiments of the present invention feature an effective amount of a bryostatin dissolved in pharmaceutically acceptable oil for oral administration for the treatment of neuro-degenerative disease. As used herein, the term "pharmaceutically acceptable oil" refers to oils which are reasonably well tolerated for oral ingestion in small amounts of 5 to 10 milliliters. Embodiments of the present invention feature olive oil. Other embodiments comprise, by way of example, without limitation include, cotton seed oil, cod liver oil, castor oil, safflower oil, peanut oil, sesame oil, corn oil, vegetable oils, oils originating with animals, and other oils commonly used in the food industry. The oil is preferably administered in a gel cap.

An effective amount of Bryostatin for humans is about 0.1 to 3.0 mg per day in the pharmaceutically acceptable oil and approximately 100 micrograms to 2 mg per day as in the microsphere.

Further embodiments of the article of manufacture comprise a retinoid dissolved in pharmaceutically acceptable oil for oral administration for the treatment of neurodegenerative disease, cancer and viral latencies. Preferably, the pharmaceutically acceptable oil has the retinoid bioavailable in an oral form and selected from the group comprising retinoic acid, retinol, retinol acetate, retinol palmitate, 13-cis-retinoic acid, and bexarotene. The Examples will feature the retinoid, retinoic acid. The Examples feature the retinoid in an amount to increase expression of alpha secretase. For example, without limitation, the retinoid is present in a dose of 1.0-240 mg per day.

Further embodiments of the article of manufacture comprise a bryostatin and retinoid dissolved in pharmaceutically acceptable oil for oral administration for the treatment of neuro-degenerative disease, cancer, viral latencies and optical diseases.

A further embodiment of the present invention is directed to a method of treating neurodegenerative disease, cancer, viral latency and/or optical diseases comprising the steps of administering orally an effective amount of a bryostatin dissolved in pharmaceutically acceptable oil.

Thus, as a treatment for neurodegenerative diseases, embodiments of the present invention feature dosage forms and methods for the oral administration of an effective amount of a bryostatin with and without a retinoid. These and other features and advantages of the present invention will be apparent upon reading the text of the detailed description below as well as viewing the accompanying drawings.

DETAILED DESCRIPTION OF THE INVENTION

Embodiments of the present invention will be described with respect to single and combination therapy, drug delivery system, dosage form and method for the treatment of neuro-degenerative diseases exemplified by Alzheimer's disease, with the understanding that the discussion relates to other neuro-degenerative diseases as well, cancers such as prostate cancer and viral latencies such as HIV and herpes. This discussion will feature the preferred embodiments of the invention with the understanding that features of the invention are capable of modification and alteration without departing from the teaching.

Figure 1:
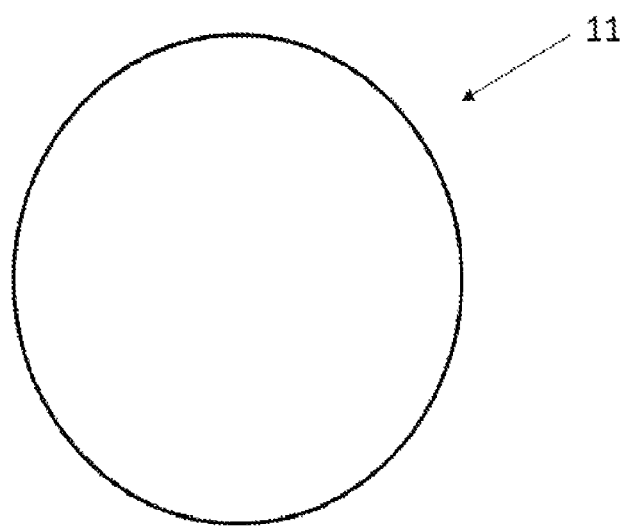
FIG. 1 depicts a microsphere embodying features of the present invention.

Turning first to FIG. 1, a microsphere, generally designated by the numeral 11 embodying features of the present invention is depicted. The microsphere 11, when combined with an adequate number of like microspheres comprises an effective dose of a bryostatin in a biopolymer. Each microsphere 11 has a diameter of one to 1000 nanometers. Although depicted as a microsphere, the article of manufacture may have an irregular shape, roughness, or be filamentous in form.

As used herein, the term "a bryostatin" refers to any and all bryostatins and Bryoids and derivatives thereof. Bryostatins and Bryoids are isolated in accordance with Castor, U.S. Pat. No. 5,750,709 and Castor "Supercritical fluid Isolation of Bryostatin-1, Phase II Final Report, SBIR Grant No. 5 R44 CA64017-03, Apr. 21, 2001.

Certain examples feature a bryostatin that is bryostatin-1. Bryostatin-1 is well characterized in the art and the structure of such compound need not be reproduced here. Several bryostatins of high potency are bryostatin-3 and first bryostatin, second bryostatin and third bryostatin referenced previously and the subject of the co-pending patent application incorporated by reference.

The bryostatin is administered in an amount to stimulate the production of alpha secretase. For example, bryostatin is administered in a dose of 0.1-50 micrograms per square meter of surface area per week. Another embodiment of the present invention features a bryostatin administered in a dose of 5-10 micrograms per square meter of surface area per week.

In embodiments which feature the co-administration of a retinoid, the retinoid is present in the same biopolymer, or made separately and combined prior to administration, or administered at the same time or close in time to have a combined effect with the bryostatin.

The retinoid is bioavailable in an oral form and selected from the group comprising retinoic acid, retinol, retinol acetate, retinol palmitate, 13-cis-retinoic acid, and bexarotene. Retinoic acid is available as an orally administered drug and is sold under the pharmaceutical name Tretinoin and tradename Retin-A®. Without being bound to a particular theory, it is believed that the retinoid acts synergistically with the bryostatin to increase expression of alpha secretase. For this purpose, the retinoid is administered in a dose of 1.0-240 mg per day.

Embodiments of the present invention feature a biopolymer resistant to acid. For the purpose of the present discussion, resistance to acid refers to stomach acid at a pH of approximately 1 to 3 for a period of time of about 0.5 to 4.0 hours. One biopolymer is a poly (D, L-lactide-coglycoside). This biopolymer has two components, a lactide and a glycoside component.

Embodiments of the present invention feature a poly (D, L-lactide-co-glycoside) having a ratio of lactide and glycoside of 25-75% lactide with the remaining comprising glycoside. A common ratio is 50:50 lactide to glycoside as determined by weight. This biopolymer is resistant to acid degradation and allows oral delivery of the drug to the small intestine for absorption.

Embodiments of the present invention feature microspheres that are lyophilized for reconstitution in an aqueous solution. Another embodiment features microspheres held in suspension for oral administration and/or held in an oral dosage form selected from the group of tablets, capsules, gel caps, and powders. Methods of making tablets, capsules, gel caps and powders are well known in the art. (Remington, 'The Science and Practice of Pharmacy'—$20^{th}$ Edition Lippincott, Williams and Williams). Suspensions for oral administration are preferably flavored to improve patient acceptance.

Another embodiment of the present invention features pharmaceutically orally acceptable oil containing an effective amount of bryostatin. An amount of oil for administration is determined, and an effective amount of bryostatin is dissolved in such oil in a manner known in the art. Preferably, the amount of oil which is intended for oral administration is enclosed in a gel cap in a manner known in the art. For example, Vitamin D and Vitamin E supplements are often enclosed in gel cap formulations.

The present method and apparatus will be described with respect to FIG. 2 which depicts in schematic form a polymer sphere apparatus, generally designated by the numeral 13. The polymer sphere apparatus is comprised of the following major elements: a polymer vessel 15, a Bryostatin drug injection assembly 17, an admixture chamber 19, a depressurization vessel 21, and an orifice nozzle 23.

Polymer vessel 15 is in fluid communication with a supercritical critical or near critical syringe pump 25 via conduits 27a, 27b and 27c. Supercritical, critical or near critical pump 25 is in fluid communication with a source of supercritical, critical or near critical fluid.

Polymer vessel 15 is also in fluid communication with a modifier syringe pump 31 via conduit 33 which intersects with conduit 27a at junction 35. Modifier syringe pump 31 is in communication with a source of modifiers and/or entrainers (not shown).

Polymer vessel 15 is loaded with polymer. This polymer vessel receives supercritical, critical or near critical fluid from supercritical critical or near critical pump 25 via conduits 27a, 27b and 27c. Polymer vessel 15 receives modifiers and/or entrainers from modifier pump 31 via conduit 33. Polymer is dissolved in the supercritical, critical or near critical fluid and modifier to form a polymer solution. Formation of the polymer solution is facilitated by circulating the polymers and supercritical, critical or near critical fluid in a loop with a conduits 27d, 27d, 27e, 27f, and 27g, a master valve 29, a static mixer 31, and a circulation pump 33.

Polymer vessel 15 is in fluid communication with admixture chamber 19 via conduits 37 and 39. Admixture chamber 19 is also in fluid communication with bryostatin drug injection assembly 17. Bryostatin drug injection assembly 17 comprises bryostatin drug syringe pump 43, a source of a bryostatin 41 and conduit 45. Bryostatin drug syringe pump 43 is in communication with a source of bryostatin material and pressurizes and compels such material through conduit 45. Conduit 45 is in communication with admixture chamber via conduits 39 which intersects conduit 45 at junction 47. Preferably, junction 47 is a mixing "T".

Admixture vessel 19 is in the nature of an inline mixer and thoroughly mixes incoming streams from the polymer vessel 15 and bryostatin drug injection assembly 17. Admixture vessel 19 is in communication with orifice nozzle 23 via conduit 49. Orifice nozzle 23 is in the nature of a back pressure regulator and has a nozzle defining one or more orifices which discharge into depressurization vessel 21 via conduit 51. Preferably, orifice nozzle 23 controls pressure and decompression rates such that a supercritical critical or near critical carbon dioxide enters the orifice at a rate of about 0.425 mls/min and 0.075 mls/min acetone or about 0.5 mls/min carbon dioxide and ethanol combined to maintain system pressure at 2,500 psig.

The operating pressure of the system can be preset at a precise level via a computerized controller (not shown) that is part of the syringe pumps. Temperature control in the system is achieved by enclosing the apparatus 11 in ¼" Lexan sheet while utilizing a Neslab heating/cooling system coupled with a heat exchanger (not shown) to maintain uniform temperature throughout the system.

In operation, polymeric materials are first packed into the polymer vessel 15. Supercritical critical or near critical fluid and an ethanolic solution of one or more bryostatin compounds are charged into the supercritical, critical or near critical syringe pumps 25 and 31, respectively, and brought to the desired operating pressure. In the alternative, an ethanol solution of one or more bryostatin compounds is charged into bioactive syringe pump 43.

In formulations featuring one or more bryostatin compounds and one or more retinoid compounds, supercritical critical or near critical fluid and an ethanolic solution of bryostatin and a retinoid compounds are charged into the supercritical, critical or near critical syringe pumps 25 and 31, respectively, and brought to the desired operating pressure. In the alternative, an ethanol solution of bryostatin and retinoid compounds is charged into bioactive syringe pump 43.

The system is pressurized with the supercritical critical or near critical fluid via supercritical, critical or near critical syringe pump 25 to the pressure level equal to that set in modifier syringe pump 31 and bioactive syringe pump 43, and maintained at this level with the nozzle orifice 23. The dynamic operating mode for all pumps is set so that each pump can be operated at its own desired flow rate. The supercritical critical or near critical stream flows through the polymer vessel 15, dissolves polymer and contacts the one or more bryostatin compounds, or one or more bryostatin and retinoid compounds, stream at junction 47. The mixture of supercritical critical nears critical fluid, bryostatin drug, or bryostatin and retinoid, or retinoid alone and polymer materials is then passed through admixture chamber 19 for further mixing. Finally, the mixed solution enters orifice nozzle 23 and is injected into a 10% sucrose solution containing 0.1% polyvinyl alcohol, 40% ethanol with trace acetic acid in the depressurization vessel 21. As a result of supercritical fluid decompression, polymer spheres containing one or more bryostatin compounds, or polymer spheres containing one or more bryostatin and retinoid compounds, or polymer compounds containing retinoid compounds are formed in the 10% sucrose solution, 0.1% polyvinyl alcohol, 40% ethanol with trace acetic acid. The expanded supercritical fluid exits the system via a vent line on the depressurization vessel 21.

The polymer nanospheres are in the nature of microspheres 11. These microspheres 11 are frozen at −80° degrees Centigrade and lyophilized.

EXAMPLES

Figure 3:
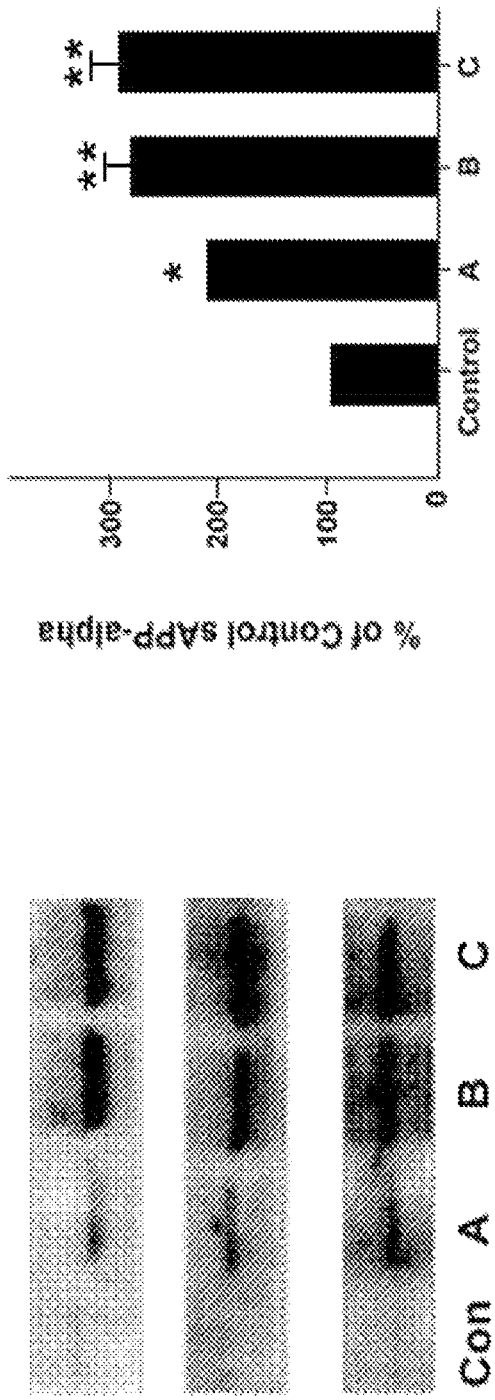
FIG. 3 shows that Bryostatin-1 induced sAPP-a formation in SH-SY5Y neuroblastoma cells is increased at 3 h by 2 µM and 4 µM retinoic acid. Retinoic acid, an inducer of ADAM10/alpha-secretase increased the generation of sAPP-a by SH-SY5Y cells. Left panel shows 6E10 western blots for sAPP-a, Right panel shows densitometric analysis. *–$p<0.05$ vs control, **–$p<0.01$ vs control, n=3.
Figure 4:
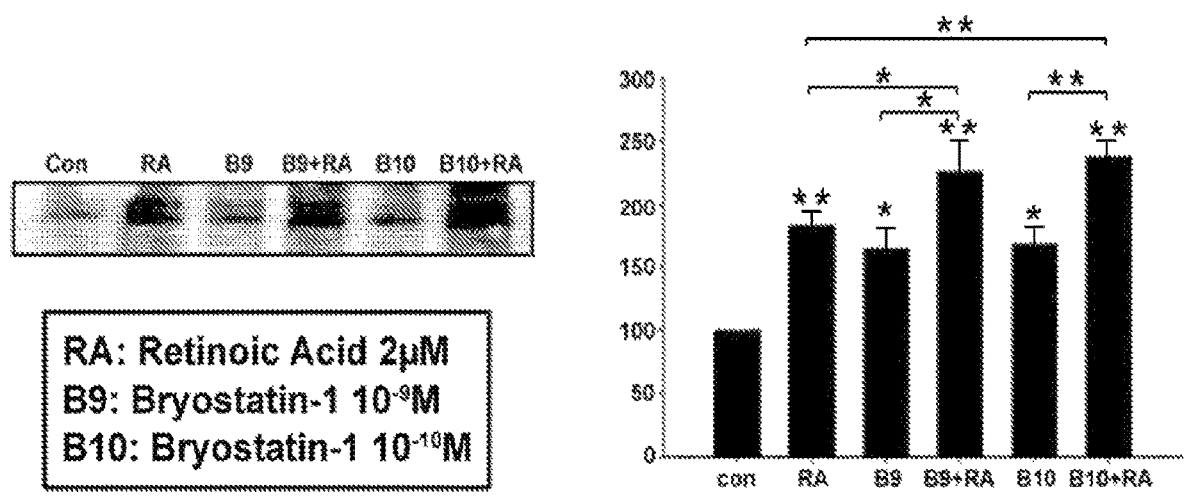
FIG. 4 depicts the effect of retinoic acid (RA, 2 µM) and Bryostatin-1 on the level of sAPPa in SH-SY5Y cells. Cells were treated with RA, Bryostatin-1 ($10^{-9}$M)+RA, Bryostatin-1 ($10^{-10}$M), RA+Bryostatin-1 ($10^{-10}$M) for 3 h. Representative western blots show sAPPa recovered from culture medium. Both Bryostatin-1 and RA significantly increased sAPPa compared to control ($p<0.05$, $p<0.01$). Combining RA and Bryostatin-1 significantly increased sAPPa recovered from culture medium.

Retinoic acid enhances Bryostatin-1 mediated alpha secretase activity. FIG. 3 shows that Bryostatin-1 induced sAPP-a formation in SH-SY5Y neuroblastoma cells is increased at 3 h by 2 μM and 4 μM retinoic acid. Retinoic acid, an inducer of ADAM10/alpha-secretase increased the generation of sAPP-a by SH-SY5Y cells. Left panel shows 6E10 western blots for sAPP-a, Right panel shows densitometric analysis. *−$p<0.05$ vs control, **−$p<0.01$ vs control, n=3; and Because Bryostatin-1 was able to enhance memory and cognition in our AD model, and was able to potently stimulate the activity of alpha-secretase in SH-SY5Y neuroblastoma cells, we investigated whether co-treatment of these cells with retinoic acid (RA, 2 or 4 uM) to increase a-secretases (ADAM10, and (and possibly ADAM17, -9, -19) expression should lead to enhanced overall APP processing. In fact we did find that SH-SY5Y cells, which were treated with both Bryostatin-1 and 2 μM or 4 μM RA showed greater sAPP-a release (measured by sAPP-α release).

Bryostatin-1 plus retinoic acid 2 μM (red bar) or 4 μM (blue bar) retinoic acid (RA) for 24 h showed an enhanced alpha secretase processing of APP to sAPP-α. These findings show that co-treatment of neuron cultures with RA plus Bryostatin-1 exhibit enhanced APP processing to sAPP-α and suggest that in vivo combinations of RA with Bryostatin-1 may synergistically enhance α-secretase activation (FIG. 1).

This data here suggest that RA plus Bryostatin-1 represent an innovative combination which (1) increases alpha-secretase levels and (2) activates the more abundant alpha-secretase to (3) achieve higher overall levels of APP processing to sAPP-α

Retinoic Acid Plus Bryostatin-1

Figure 2:
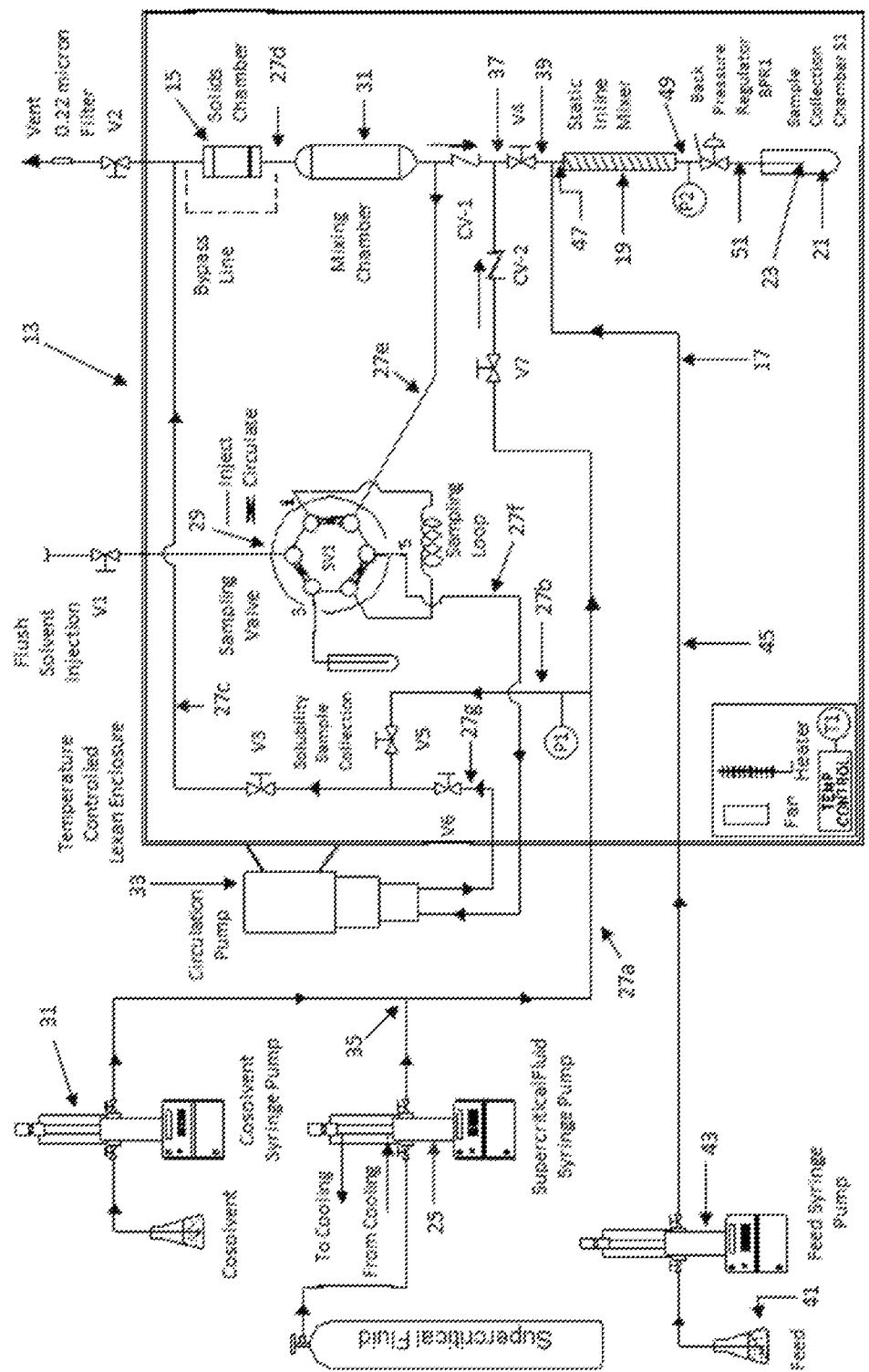
FIG. 2 depicts an apparatus for making one or more microspheres of the present invention.

FIG. 2 shows that in SH-SY5Y neuroblastoma cells, sAPP☐ formation is increased by 2 µM retinoic acid (p<0.01) similar to $10^{-9}$M Bryostatin-1. An additive effect was observed when retinoic acid (RA) was added at 2 µM concentration with Bryostatin-1 at $10^{-9}$M and $10^{-10}$M.

Interestingly, FIG. 2 shows that both RA and Bryostatin-1 can each significantly increase expression of ADAM10 (the major form of ☐-secretase) and that in combination there is at least an additive effect on expression. This would be the first demonstration that Bryostatin-1 increases the expression of ☐-secretase, which is a novel and unanticipated effect of Bryostatin-1. Therefore, Bryostatin-1 may increase ☐-secretase processing through 2 independent mechanisms: (i) activation of PKCs which stimulate☐☐☐secretase; and (ii) increased expression of ☐-secretase.

It is also possible that the increased abundance of ADAM10 might reflect increased ADAM10 stability and not necessarily greater protein synthesis. In any case, the effect on ADAM10 is novel. ADAM10 mRNA synthesis may be increased by Bryostatin-1 ultimately leading to greater α-secretase.

Oil Based Bryostatin Solutions

Oil based bryostatin solutions are made with the desired amount of bryostatin dissolved in olive oil with vitamin E as a preservative and lecithin and medium chain triglyceride emulsifiers to increase bioavailability. The oil with the dissolved bryostatin is encapsulated in gel capsules with a nitrogen purge and head. In the alternative, the oil with dissolved bryostatin is administered as a liquid dosage form. In the alternative, the oil with dissolved bryostatin may also be emulsified and administered as a liquid formulation. Emulsification may mask some of the less desirable taste and texture associated with oil based oral formulations.

Oil based Bryostatin and Retinoic acid Solutions

Oil based bryostatin and retinoic acid solutions are made with the desired amount of bryostatin and retinoic acid dissolved in olive oil with vitamin E as a preservative and lecithin and medium chain triglyceride emulsifiers to increase bioavailability. The oil with the dissolved bryostatin and retinoic acid is encapsulated in gel capsules with a nitrogen purge and head. In the alternative, the oil with dissolved bryostatin and retinoic acid is administered as a liquid dosage form. In the further alternative, the oil with dissolved bryostatin and retinoic acid may also be emulsified and administered as a liquid formulation. Emulsification may mask some of the less desirable taste and texture associated with oil based oral formulations.

Bryostatin Microspheres

Microspheres comprising polymers and bryostatin 1 were prepared in accordance with the methods described above. The results are summarized in Table 1 below.

TABLE 1

Summary of Polymer Nanoencapsulation of Bryostatin-1 Experiments

| Expt. No. | SFS | P (bars) | T (° C.) | Particle Size (nm) | Bryo-1 (mg/ 100 mls) | Encap- sula- tion (%) |
|---|---|---|---|---|---|---|
| ALZ-01-01 | $CO_2$:Acetone::95:5 | 171 | 45 | 259 | 0.0511 | 11.4 |
| ALZ-02-01 | Freon-22 | 205 | 22 | 973 | 0.3089 | 16.8 |
| ALZ-03-01 | $CO_2$:Ethanol::85:15 | 171 | 45 | 246* | 0.0027 | 71.3 |
| ALZ-04-01 | $CO_2$:Acetone::95:5 | 171 | 45 | 215* | 0.0160 | 50.8 |
| ALZ-05-01 | $CO_2$:Acetone::95:5 | 171 | 45 | 254* | 0.1323 | 84.0 |
| ALZ-06-01 | $CO_2$:Acetone::85:15 | 171 | 45 | 251* | 0.2374 | 82.3 |

*After lyophilization and reconstitution

The nanospheres appear stable at 4-25° C. (Centigrade) for at least one week duration. Further, the nanospheres appear stable in solutions at about pH 1.13 at 37° C. (Centigrade), similar to a stomach environment.

Results further suggest that nanospheres with bryostatins and bryostatin 1, in particular, induce alpha-secretase processing of amyloid precursor protein (APP) to s-APP alpha, and activate protein kinase C (PKC) isoforms alpha, delta and epsilon (measured by membrane translocation) in the SH-SY5Y neuroblastoma cell line. These events are well-described cell and pharmacological events associated with prevention of beta-secretase mediated formation of beta-amyloid, the presumptive cause of dementia in human Alzheimer's disease and in the sweAPP/PS1 mouse model of Alzheimer's disease.

Bryostatin and Retinoid Microspheres

Microspheres comprising polymers and one or more bryostatin and retinoid compounds are prepared in accordance with the methods described above.

Water Maze Studies

Mouse strain B6C3-Tg carrying mutant Swedish Amyloid precursor protein (sweAPP) and PS1 (presenilin-1) genes associated with early onset Alzheimer's disease were subjected to water maze tests at 5-6 months of age. These tests suggest that mice that received bryostatin-1 at a dose of 5 micrograms/mouse on alternative days orally in an oil formulation showed significant protection against Alzheimer's disease mediated memory loss produced by the APP/PS1 mutations as compared with memory acquisition skills seen in control animals.

Therefore, we have described the present invention with respect to preferred embodiments with the understanding that these embodiments are capable of modification and alteration without departing from the teaching herein. Therefore, the present invention should not be limited to the precise details, but should encompass the subject matter of the claims that follow and their equivalents.

The invention claimed is:

1. A pharmaceutical formulation for the treatment of a neurodegenerative disease comprising:
    an effective amount of bryostatin-1;
    an effective amount of retinoid selected from the group consisting of retinoic acid, retina, retinol acetate, retinol palmitate, 13-cis-retinoic acid, and bexarotene; and
    a plurality of nanospheres, co-encapsulating the bryostatin-1 and retinoid in an effective amount to synergistically increase expression of alpha secretase, each nanosphere having a diameter in the range of one to 1000 nanometers, and wherein each nanosphere is formed of a polymer consisting of a poly (D, L-lactide-co-glycoside);
    wherein the pharmaceutical formulation increases alpha secretase activity in a subject receiving treatment.

2. The formulation of claim 1 wherein the neurodegenerative disease is selected from the group consisting of Alzheimer's Disease, Hutchinson's Disease, Parkinson's Disease, Kuru, Creutzfeldt-Jakob Disease, Down's syndrome and spongiform encephalopathies.

3. The formulation of claim 1 wherein said poly (D, L-lactide-co-glycoside) has a ratio of lactide and glycoside of 25-75% lactide to 75-25% glycoside by weight.

4. The formulation of claim 1 wherein the plurality of nanospheres is in a lyophilized form for reconstitution in an aqueous solution.

5. The formulation of claim 1 wherein said plurality of nanospheres is in an oral dosage form.

6. The formulation of claim 1 wherein the formulation of said plurality of nanospheres is in an oral dosage form selected from the group consisting of tablets, capsules, gel caps, and powders.

7. The formulation of claim 1 wherein the plurality of nanospheres is formed in a polymer nanosphere apparatus comprising
   a polymer vessel;
   a drug injection assembly;
   an admixture chamber;
   a depressurization vessel; and
   an orifice nozzle.

8. The formulation of claim 1, wherein the plurality of nanospheres is formed by decompressing a supercritical or near critical polymer fluid containing the bryostatin-1 and retinoid.

9. A formulation for the treatment of one or more diseases that respond to increases in alpha secretase activity comprising
   an effective amount of a byostatin-1 and an effective amount of retinoid; and
   wherein the bryostatin and the retinoid are encapsulated in a plurality of biopolymer nanospheres having a diameter of one to 1000 nanometers, wherein the said biopolymer is a poly (D,L-lactide-co-glycoside), and wherein the bryostatin-1 and the retinoid are co-encapsulated in an effective amount to synergistically increase expression of alpha secretase.

10. The formulation of claim 9 wherein said retinoid is retinoic acid.

11. The formulation of claim 9 wherein said biopolymer is resistant to acid.

12. The formulation of claim 9 wherein said poly (D, L-lactide-co-glycoside) has a ratio of lactide and glycoside of 25-75% lactide by weight with the remaining comprising glycoside.

13. The formulation of claim 9 wherein said plurality of nanospheres is in a lyophilized form for reconstitution in an aqueous solution.

14. The formulation of claim 9 wherein said plurality of nanospheres is held in an oral dosage form selected from the group consisting of tablets, capsules, gel caps, and powders.

15. The formulation of claim 9, wherein the one or more diseases is selected from the group consisting of neurodegenerative disease, viral latency disease, and ophthalmic disease.

16. The formulation of claim 9, wherein said one or more diseases is selected from the group consisting of Alzheimer's Disease, Hutchinson's Disease, Parkinson's Disease, Kuru, Creutzfeldt-Jakob Disease, Down's syndrome and spongiform encephalopathies.

17. The formulation of claim 9, wherein said one of more diseases is a viral latency disease associated with human immunodeficiency virus (HIV) or herpes.

18. The formulation of claim 9, wherein said effective amount of bryostatin-1 is present for administration in a dose of 3-10 micrograms per kilogram of body weight per day.

* * * * *